United States Patent [19]

Weinberg et al.

[11] Patent Number: 5,431,689
[45] Date of Patent: Jul. 11, 1995

[54] IMPLANTABLE STIMULATION SYSTEM AND METHOD FOR TERMINATING CARDIAC ARRHYTHMIAS

[75] Inventors: Lisa P. Weinberg, Moorpark; Jason A. Sholder, Beverly Hills, both of Calif.

[73] Assignee: Pacesetter, Inc., Sylmar, Calif.

[21] Appl. No.: 125,971

[22] Filed: Sep. 23, 1993

[51] Int. Cl.⁶ .............................................. A61N 1/36
[52] U.S. Cl. ..................................................... 607/14
[58] Field of Search ........................... 607/14, 9, 27, 15

[56] References Cited

U.S. PATENT DOCUMENTS

| | | | |
|---|---|---|---|
| 3,942,534 | 3/1976 | Allen et al. | 128/419 PG |
| 3,949,758 | 4/1976 | Jirak | 128/419 PG |
| 4,312,356 | 1/1982 | Sowton et al. | 128/419 PG |
| 4,390,021 | 6/1983 | Spurrell et al. | 128/419 PG |
| 4,398,536 | 8/1983 | Nappholz et al. | 128/419 PG |
| 4,406,287 | 9/1983 | Nappholz et al. | 128/419 PG |
| 4,408,606 | 10/1983 | Spurrell et al. | 128/419 PG |
| 4,427,011 | 1/1984 | Spurrell et al. | 128/419 PG |
| 4,541,430 | 9/1985 | Elmqvist et al. | 128/419 PG |
| 4,561,442 | 12/1985 | Vollmann et al. | 128/419 PG |
| 4,574,437 | 3/1986 | Segerstad et al. | 128/419 PG |
| 4,577,633 | 3/1986 | Berkovits et al. | 128/419 PG |
| 4,726,380 | 2/1988 | Vollmann et al. | 128/419 PG |
| 4,872,459 | 10/1989 | Pless et al. | 128/419 PG |
| 5,103,822 | 4/1992 | Duncan | 607/15 |
| 5,144,947 | 9/1992 | Wilson | 607/15 |

OTHER PUBLICATIONS

Sowton, Edgar, "Clinical Results with the Tachylog Antitachycardia Pacemaker," *PACE*, vol. 7, pp. 1313–1317 (Nov.–Dec. 1984 Part II).
Vallin, H. O., "Centrifugal Geometric Scanning—an Alternative Concept in Pacemaker Treatment of Tachycardias," *Cardiac Pacing*, pp. 809–814 (1983).
Siemens *Tachylog 651 B and 651 L Physician's Manual* (Nov. 1984). (complete manual, pp. 1–80).

*Primary Examiner*—William E. Kamm
*Assistant Examiner*—Kennedy J. Schaetzle
*Attorney, Agent, or Firm*—Lisa P. Weinberg

[57] ABSTRACT

A cardiac arrhythmia is terminated by stimulating the heart during the narrow "region of susceptibility" or termination window of the arrhythmia cycle based upon a statistically significant starting value. The present invention will store a plurality of successful critically timed intervals and compute a central value (e.g., average, mean, median, etc.) and a measure of variability (sample range, standard deviation, etc.). The measure of variability is used to determine the termination window size. In one embodiment, the present invention then "scans" symmetrically-centrifugally about the statistically significant starting value. In an alternate embodiment, the present invention employs ranked scanning, that is, scanning according to the frequency of occurrence of previously successful starting values. The number and size of steps could be either programmable, or automatically computed by the pulse generator based upon the termination window size. With each successful termination, the statistically significant starting value is updated, thereby providing an intelligent stimulation device which can adapt itself to the patient's ever-changing needs. Histograms of the data could also be displayed on a screen so that the physician could quickly verify the appropriateness of the computed central value and range.

51 Claims, 2 Drawing Sheets

IMPLANTABLE STIMULATION SYSTEM AND METHOD FOR TERMINATING CARDIAC ARRHYTHMIAS

FIELD OF THE INVENTION

The present invention relates to implantable cardiac stimulation systems, and more particularly, to an improved implantable cardiac stimulation device and method for statistically determining a starting value and sequence for terminating an arrhythmia, and to an external programming device for displaying such statistical data.

BACKGROUND OF THE INVENTION

A tachycardia is an arrhythmia in which the heart beats at an abnormally rapid rate, inappropriate for the tissue involved and inappropriate for metabolic need. Tachycardias usually have a rate greater than 100 beats per minute (bpm), but may be less, such as in junctional tachycardias which include any junctional rhythm faster than 60 beats per minute. Tachycardias are typically classified as being supraventricular or ventricular. Supraventricular refers to an arrhythmia whose origin is above the ventricles, such as sinus tachycardia, atrial flutter, and atrial fibrillation.

Cardiac stimulation has been utilized for many years for the purpose of terminating intrinsic atrial and/or ventricular tachycardias. An implantable stimulation device which is capable of treating tachycardias through the application of stimulation pulses, or antitachycardia pacing, is sometimes referred to as an "antitachycardia pulse generator" or an "antitachycardia pacemaker." Antitachycardia pulse generators typically are only used for supraventricular tachycardias.

If the implantable stimulation device further includes the ability to detect and treat ventricular tachycardia and ventricular fibrillation, the device is often referred to as an "antitachycardia defibrillator," an "implantable cardioverter defibrillator (ICD)," or simply a "defibrillator." Although the early defibrillators only provided shock therapy for treating ventricular fibrillation, modern defibrillators typically include both antitachycardia pacing and cardioverter/defibrillator shock therapy. As used herein, an implantable stimulation device includes any stimulation device capable of delivering stimulation pulses to disrupt an arrhythmia.

The underlying principle of using stimulation pulses to terminate a tachycardia is based on the premise that if an implantable stimulation device delivers a stimulation pulse to the heart during a critical time period following a naturally occurring heartbeat, the heart may revert to sinus, or natural, rhythm. This is best understood by reviewing the mechanism causing the arrhythmia. A tachycardia is often the result of an electrical feedback mechanism within the heart. For example, a natural heartbeat can occur through a normal pathway and re-enter through an alternate loop of tissue that perpetuates conduction (also known as an accessory or re-entrant pathway), thereby initiating a tachycardia. The delivery of a stimulation pulse causes the cardiac tissue in front of the stimulation pulse to depolarize (thereby causing the heart to contract), but leaves the tissue at the stimulation site refractory (i.e., the tissue cannot respond to additional stimulation). Thus, by injecting a stimulation pulse within the cardiac cycle, the stability of the feedback loop is disrupted, and the heart may revert to a natural sinus rhythm.

The difficulty in using a stimulation pulse to terminate a tachycardia lies in determining exactly when the stimulation pulse should be applied. It must be applied at a time shortly following one heartbeat and prior to the time when the next heartbeat would otherwise occur. On an ECG recording, this would correspond to the interval between successive R-waves.

It is known that there is usually a "region of susceptibility" within a given tachycardia cycle during which the heart is susceptible to reverting back to a sinus rhythm through the application of a stimulation pulse to the heart. This critical time period may be thought of as an arrhythmia "termination window." The terms "region of susceptibility" and "termination window" are used interchangeably herein to refer to this narrow time period.

Unfortunately, the size of the termination window (that is, the length of time available to successfully interrupt the re-entrant pathway) depends on the tachycardia rate, the length of the reentrant pathway, and the refractory periods of tissue in the pathway. The termination window may further be altered by body posture, physiological conditions, antiarrhythmic drug therapy, physical activities, diurnal cycles, catecholamine levels, and numerous other factors which affect conduction velocity and refractory characteristics of cardiac tissue. The termination window further varies not only from patient to patient, but from day to day for the same patient. Moreover, for any given patient on any given day, the termination window within the overall tachycardia cycle is relatively short and may vary even during a single tachycardia episode.

In order to increase the likelihood that a stimulation pulse will be applied during the region of susceptibility and therefore likely to be successful in terminating an arrhythmia, it is known in the art to use several techniques to "hunt" for and find the termination window. Typically, heretofore, the manner in which the "hunting" for the termination window has been accomplished, follows either one of two approaches: (1) "shotgunning" the termination window by applying a burst of stimulation pulses; or (2) "scanning" the termination window by delivering "critically timed" stimulation pulses.

The theory behind providing a burst of pulses is that sooner or later one of the stimulating pulses will occur at a time in the tachycardia cycle which will terminate the tachycardia. Burst pacing may be delivered asynchronously or synchronously at a fixed, decreasing, or increasing, cycle length. This process continues until the region of susceptibility is found, and the tachycardia is terminated. Once the region of susceptibility is found, the timing associated with the successful burst may be stored and used as the starting point for applying a new burst of simulation pulses to the heart upon the next occurrence of a tachycardia. Prior art representative of this shotgun (burst pacing) approach of terminating a tachycardia can be found in U.S. Pat. Nos. 4,398,536 (Nappholz et al.); 4,406,287 (Nappholz et al.); 4,408,606 (Spurrell et al.); 4,541,430 (Elmqvist et al.); and 4,561,442 (Vollmann et al.).

The alternate technique to find the termination window is by "scanning." This technique utilizes an implantable stimulation device which automatically searches or "scans" for the pacing interval most likely to terminate a tachycardia. The implantable stimulation device delivers single or multiple stimulation pulses at "critically timed" coupling intervals (that is, intervals coupled to the last R-wave to terminate a tachycardia) and continues in a controlled sequence until the tachycardia terminates. For example, the controlled sequence may begin with a single stimulation pulse at one end of the scanning window and, with each successive tachycardia cycle, deliver additional pulses at increasing (or decreasing) coupling intervals in a controlled manner towards the other end of the window. Hence, the stimulation pulse scans through the scanning window looking for the region of susceptibility.

For example, in U.S. Pat. No. 4,312,356 (Sowton et al.), a pulse generator is disclosed wherein the sensing of a tachycardia triggers a stimulation pulse having a known and somewhat arbitrary timing relative to the tachycardia cycle. The stimulation pulse is thus applied to the heart at a time within the cardiac cycle that represents a first guess of the timing of the region of susceptibility. If the stimulation pulse is not successful in terminating the tachycardia, then a subsequent stimulation pulse is provided, issued either later or earlier (according to a predetermined search pattern) relative to the timing of the unsuccessful stimulation pulse. In this trial-and-error manner, the region of susceptibility is eventually located, and the tachycardia is terminated. Unfortunately, this approach may require a significant "hunting" time before the region of susceptibility is located.

In order to shorten the hunting time, it is also known in the art to store the time interval associated with the last successful stimulation pulse. This last successful time interval is then used as a starting point for the scanning window when the next tachycardia occurs. In this manner, the "hunting" time is believed to be significantly reduced. The prior art approaches using a pulse that hunts for the region of susceptibility by scanning through a scanning window can be found in U.S. Pat. Nos. 4,390,021 (Spurrell et al.) and 4,427,011 (Spurrell et al.). U.S. Pat. No. 4,577,633 (Berkovits et al.) accomplishes essentially the same result (of providing a single scanning stimulation pulse that hunts for the region of susceptibility) by continuously shortening the pulse generator escape interval with each subsequent beat, for a predetermined number of beats, by a small programmable decrement.

It is also known in the art to combine shotgunning (burst pacing) and single-pulse scanning as selectable options within a single pulse generator (U.S. Pat. No. 4,726,380 (Vollmann et al.)).

Burst pacing has been very successful in terminating cardiac arrhythmias and was initially the preferred approach. However, in some cases, burst pacing has been known to disorganize or accelerate an arrhythmia instead of terminating it. Furthermore, it is also known that the longer it takes to terminate the arrhythmia, the more difficult the arrhythmia can be to ultimately treat.

As a result, the stimulation pulse scanning techniques are currently favored in an attempt to lessen the risk of arrhythmia acceleration while maintaining a high efficacy for arrhythmia termination. Scanning of the termination window has also been necessary in order to account for the variations in the exact timing of the tachycardia termination window that regularly occurs in any given patient.

Unfortunately, however, if the "region of susceptibility" (or termination window) has shifted in a direction that causes longer intervals for termination, the starting point of the scanning sequence may require an entire scan to be completed before finding the termination window. Depending on the total range and number of critically timed intervals, the steps or amount of adjustment within each attempt, the number of pulses, and the exact sequence to be attempted, an entire cycle of scanning may be a long process.

What is needed, therefore, is an arrhythmia termination system that prevents long periods of time in locating the region of susceptibility and improves the success rate of termination, thereby minimizing the time required to terminate the arrhythmia.

SUMMARY OF THE INVENTION

The present invention is directed toward an implantable stimulation device capable of treating a cardiac arrhythmia by stimulating the heart during a narrow "region of susceptibility" (or termination window) of the arrhythmia cycle based upon statistical analysis of a plurality of previously successful critically timed stimulation pulses. With each successful termination of the arrhythmia, the present invention statistically determines a new starting value, termination window, and scanning sequence, for a subsequently detected arrhythmia. As a result, the present invention provides a significantly higher probability of terminating the arrhythmia quickly.

At implant, a plurality of tachycardias will be induced and a plurality of successful critically timed intervals will be found by using traditional methods, for example, shotgunning, scanning and/or using the last known successful termination value.

The present invention is based on the premise that after a plurality of successful terminations have been found, a frequency distribution (also known as a histogram) of the previously successful critically timed interval will reveal a normal, "bell-curve" (Gaussian), distribution. A variety of factors which contribute to a given patient's variability of the region of susceptibility will be represented by the steepness or flatness of the distribution. The bellcurve can be characterized as having a "central value" and a "measure of variability."

As is known in the statistical art, there are several methods for calculating a "central value," including: an arithmetic mean; the midrange; the geometric mean; the median; and the mode.

By "measure of variability," what is meant is a measure of how the previously successful starting values are distributed about the central value. In a normal (Gaussian) distribution, the data points are typically distributed symmetrically about a mean value. Small deviations from the mean usually occur more often than larger differences, and larger differences occur only rarely. Standard deviation is but one method, the most common method, of predicting this distribution. Other well known methods of measuring variability which could be used with the present invention, include: the sample range and the average deviation.

Thus, the present invention includes a memory device for storing a plurality of previously successful critically timed intervals. The present invention further includes a microprocessor, or other computing circuitry, to compute a "central value" and a "measure of variability" based upon the previously successful stored values.

In the preferred embodiment, the statistically determined "central value" will be the sample-based arithmetic mean, $\overline{X}$, since this value is fairly accurate in finding the central value. In the preferred embodiment, the statistically determined "measure of variability" will be the sample-based standard deviation, s, which can in turn be used to determine a range of previously successful critically timed intervals for the termination window. For example, if three standard deviations are chosen for the termination window, then 99.7% of all of the previous successful starting values will be included in the termination window.

The number and size of steps could be either programmable, or automatically computed by the implantable stimulation device, based on the size and the distribution of the termination window. For example, since 68% of the previously successful critically timed intervals fall within one standard deviation from the mean, it may be desirable to decrease the size of the steps within one standard deviation of the central value so that more attempts are made close to the central value.

Although the preferred embodiment employs the sample-based arithmetic mean, $\overline{X}$, and the sample-based standard deviation, s, any method of calculating the "central value" and "measure of variability" could be used to determine a starting value and a termination window (or range of critically timed intervals) for a subsequent arrhythmia, and will be more statistically significant than the prior art methods of using the last known successful value. And, of course, any combination of "central value" and "measure of variability" could be used, as is best suited for the particular hardware, software and current drain constraints.

As more values are accumulated, the "central value" and the "measure of variability" will become more accurate, or more representative, of the current state of the patient. With each successful termination, the statistically determined "central value" is updated, thereby providing an "intelligent" stimulation device which can adapt itself to the patient's ever-changing needs.

In the preferred embodiment, the present invention employs scanning in a "symmetrical-centrifugal fashion," providing stimulation pulses alternately earlier and later about the statistically determined central value. A symmetrical-centrifugal scan takes advantage of the fact that the distribution of previously successful critically timed intervals is also symmetrical about the central value. Thus, a symmetrical-centrifugal scan enables other statistically significant values to be used for subsequent stimulation pulses in order of probability (from highest to lowest), unlike the prior art which employs a centrifugal scan based on an arbitrary geometric series.

In an alternate embodiment, the present invention employs "ranked scanning," that is, scanning is performed with critically timed stimulation pulses in descending order, from the highest frequency of occurrence to the lowest frequency of occurrence. In this embodiment, the termination attempt will begin at the interval corresponding to the most frequently successful critically timed interval (i.e., the mode value of the distribution) stored in memory, scanning to the second and third, etc., most frequent critically timed intervals until all previously successful values have been tried or until termination occurs.

To ensure that the system is functioning properly, histograms of the data are available to the physician and displayed on a screen so that the physician may quickly verify whether the histograms are normal (Gaussian). As is known in the statistical art, the number of class intervals necessary to produce a reasonable histogram should be no fewer than 5 and no more than 15 intervals. The simplest way to achieve this is to determine the total range and divide it into a desired number of class intervals.

The present invention further contemplates a method for terminating a cardiac arrhythmia. The method includes storing a plurality of previously successful critically timed intervals found in terminating a plurality of cardiac arrhythmias. The method of the present invention then determines a starting value and a termination window based upon a statistical analysis of the plurality of previously successful starting values. Scanning may occur in either a symmetrical-centrifugal order or a ranked order (i.e., in order of frequency from highest to lowest).

It will therefore be perceived that the advantages of the present invention result in an arrhythmia termination system and method that applies a stimulation pulse to the heart during a given cardiac cycle with a higher probability of locating the narrow termination window of the heart. Such a cardiac arrhythmia termination system and method therefore minimizes the hunt time necessary for locating the termination window, regardless of whether a single, multiple or a burst of stimulation pulses are used. By providing a higher quality of life for the patient, the system and method of the present invention provide a highly desirable enhancement to implantable cardiac pulse generator therapy.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE INVENTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Before describing the present invention, it will be helpful to understand the basic principles of centrifugal scanning, as is known in the prior art. Thus, FIG. 1 is presented to illustrate the basic principles of a pulse generator timing cycle, and FIG. 2 is presented to illustrate a centrifugal scan during the pulse generator's termination window.

A complete description of centrifugal scanning can be found in U.S. Pat. No. 4,574,437 (Segerstad and Vallin) and functionally described in "Centrifugal Geometric Scanning—An Alternative Concept in Pulse generator Treatment of Tachycardias," Vallin et al., Cardiac Pacing, pp. 809-814 (1983), both of which are incorporated herein by reference.

Figure 1:
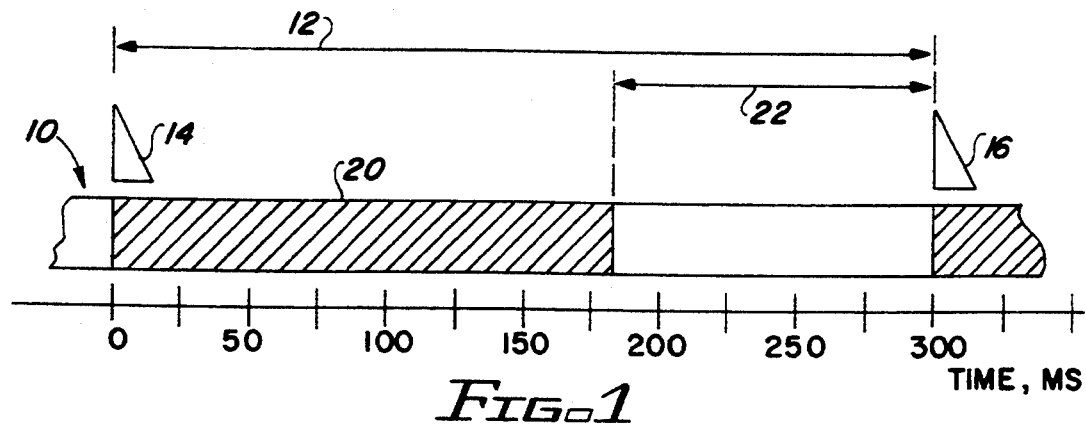
FIG. 1 depicts a timing cycle for an implantable stimulation device for a tachycardia rate of 200 bpm, and illustrates the termination window.
Figure 2:
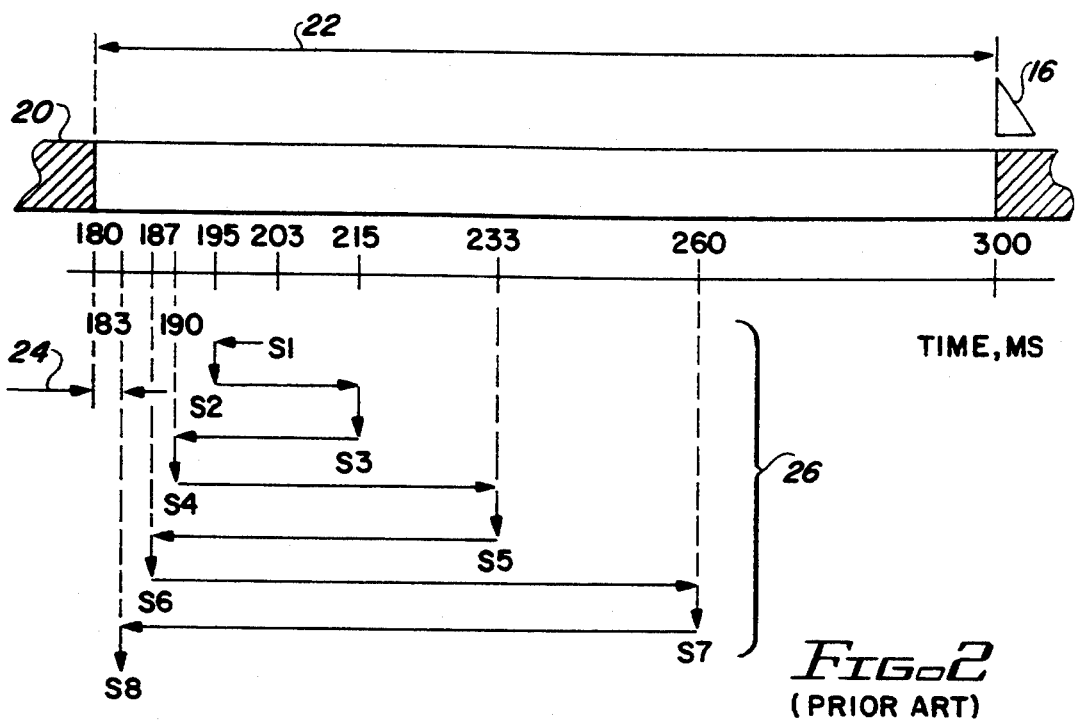
FIG. 2 depicts a magnified view of the termination window, illustrating the prior art method of centrifugal scanning.

In FIG. 1, a pulse generator timing cycle 10 is shown for one cardiac cycle of a tachycardia. By way of example, the rate of the tachycardia is shown as 200 bpm, which corresponds to a cycle length (or R—R interval) 12 of 300 ms. The right triangles 14 and 16 are used to indicate a sensed R-wave (or P-wave). A refractory period 20 is programmably selected to allow for tissue refractory periods and to prevent the pulse generator from oversensing its own stimulation pulses. In the timing cycle 10 shown in FIG. 1, the refractory period 20 is illustrated, by way of example, as 180 ms.

The basic principles of pulse generator timing cycles, the primary components of a conventional pacing system, and the basic operation thereof, are well known. For a more complete description, see U.S. Pat. Nos. 4,232,679 (Schulman); 4,686,988 (Sholder); and 4,809,697 (Causey et al.), which patents are hereby incorporated herein by reference.

An alert window 22 defines a timing window in which cardiac signals can be sensed and in which a stimulation pulse can be delivered to the heart to interrupt an arrhythmia. As used herein, a "critically timed" stimulation pulse is a stimulation pulse which is coupled to the last R-wave (at 14) and will be delivered during the alert window 22 before the next expected R-wave (at 16). The interval between an R-wave and a critically timed stimulation pulse is called a "critically timed interval."

As shown in FIG. 2, the alert window 22 is magnified and illustrates a centrifugal scanning scheme of the prior art. The prior art teaches scanning a portion of the alert window 22 starting with a stimulation pulse at a previously successful critically timed interval. If this stimulation pulse is not effective, additional critically timed intervals are attempted, alternatively earlier or later, based on a predetermined geometric series, in a centrifugal fashion until the tachycardia is terminated or a programmed number of attempts are made. A minimum delay 24 is programmed, following the refractory period 20. The interval remaining to the end of the R—R interval is partitioned into a predetermined number of steps (e.g., eight steps) according to a predetermined geometric series, decreasing each step with one third of the remaining interval. As further illustrated in FIG. 2, if the last successful value was, for example, 203 ms, the first critically timed stimulation pulse, S1, would also be 203 ms. If the first stimulation pulse was unsuccessful, a second critically timed stimulation pulse, S2, would be delivered followed by S3, S4, S5, etc., according to the geometric series. The result is a centrifugal scan 26, shown in FIG. 2.

The prior art (Vallin et al.) further discloses that the termination zone is deemed to be more often located soon after the refractory period than later in the R—R interval.

Thus, the disadvantages of the prior art are: (1) the last value may not necessarily be the ideal starting value for the next tachycardia detected; (2) different tachycardia rates may have a different termination windows; (3) the step sizes are arbitrary and can miss the critical interval entirely; and (4) the stimulation pulses are not concentrated soon after the refractory period, but rather scattered across the whole alert window. Furthermore, the prior art will not update the starting value until a new successful value is found, even if it proves to be ineffective later on.

Since the present invention is based on statistical analysis of a sampled population and because there are several "data descriptors" (i.e., calculated variables) which are frequently used to described the characteristics of the sampled population, it will be beneficial to review the basic statistical formulas and principles before describing the present invention.

When a frequency distribution or histogram is constructed of a large number of measurements, a familiar "bell-curve" often results. This bell-curve is known as the Gaussian distribution, described by and named after the mathematician Gauss.

There are two basic types of data descriptors. The first data descriptor is a calculated value to describe the "central value" of the distribution. When accumulating data for statistical analysis, it is a common observation that the samples within a sizable body of data will tend to cluster around some central value. The most common data descriptors for determining the central value include: the arithmetic mean; the midrange; the geometric mean; the median; and the mode.

The most commonly used data descriptor for determining the central value is the average, the arithmetic mean, or simply the mean. Data points are typically distributed symmetrically about the mean value. The sample-based arithmetic mean, $\overline{X}$, is an estimate of the mean value for the whole population $\mu$ and is given by the formula shown below.

$$\text{Mean}, \overline{X} = \frac{\Sigma X_i}{n}$$

The midrange, MR, is defined as the average of the largest and the smallest value and could also be used as an estimate of the population mean, $\mu$. Although the midrange provides ease of calculation, it is sensitive to extreme values in the tails of the distribution. The formula for the midrange is shown below, where $X_{min}$ is the minimum sample value and $X_{max}$ is the maximum sample value.

$$\text{Midrange}, MR = \frac{(X_{min} + X_{max})}{2}$$

A geometric mean is sometimes a more appropriate data descriptor. It is the calculated $n^{th}$ root of the product of n data points.

$$\text{geometric mean} = (X_1)(X_2)(X_3)\ldots(X_n)^{1/n}$$

In small data sets, the median (or middle) value may be a better choice. The median is obtained by first lining up the individual data points in the order of their numerical value. In the case of an odd number of points, the middle value is the median. In the case of an even number of points, the average of the two points straddling the center is the median. Its use minimizes the influence of unbalance due to extreme values in the calculation of the mean. The mean and the median are identical for a normal distribution, but can differ considerably when using small sample sizes.

$$\text{Median, } M = \left[ \frac{n+1}{2} \right]^{th} \text{ observation}$$

(when the values are arrayed in order of magnitude)

Another data descriptor is the mode, which is the value occurring most frequently in the data set, usually but not always located somewhere near the center. There can also be several modes in a set of data, resulting from the fact that they represent several populations. The mode value may be more insightful in revealing different re-entrant mechanisms.

It is clear that knowing the central value is not sufficient alone to describe the population, or samples, adequately. Thus, the second data descriptor is a "measure of variability," or dispersion, among the sampled values. Thus, the present invention contemplates using one of the three most common methods of measuring variation: the sample range; the average deviation; and the standard deviation.

The simplest measure of variability is the sample range, R, that is, the difference between the largest and the smallest value in the sample. Like the midrange, the sample range is most effective and easiest to compute when the small samples are the rule (n<10). The formula for the sample range is shown below, where $X_{min}$ is the minimum sample value and $X_{max}$ is the maximum sample value.

$$\text{Sample Range, } SR = X_{min} - X_{max}$$

The sample range, SR, could be used in one of two ways. Firstly, the sample range could be centered about the desired central value. Secondly, the lower and upper limits could be simply $X_{min}$ and $X_{max}$. The latter may be advantageous if the histogram is skewed to one side.

While the sample range involves only the smallest and largest values, the average deviation, AD, also includes a measure of the intermediate observations. The average deviation is defined as the arithmetic average of the absolute values of the differences between the individual observations and their arithmetic mean. The formula for the average deviation is shown below, $$\text{Average Deviation, } AD = \frac{\sum_{i=1}^{n} |x_i|}{n}$$

where a deviation from the mean is $x_i = X_i - \overline{X}$.

Perhaps the most widely used measure of variability is the standard deviation, $\sigma$, so named because it describes the dispersion of a normal population. The sample-based standard deviation, s, is an estimate of the population standard deviation $\sigma$ and is given by the formula shown below.

$$\text{Sample-based Standard Deviation, } s = \sqrt{\frac{\Sigma(X_i - \overline{X})^2}{n - 1}}$$

Figure 3:
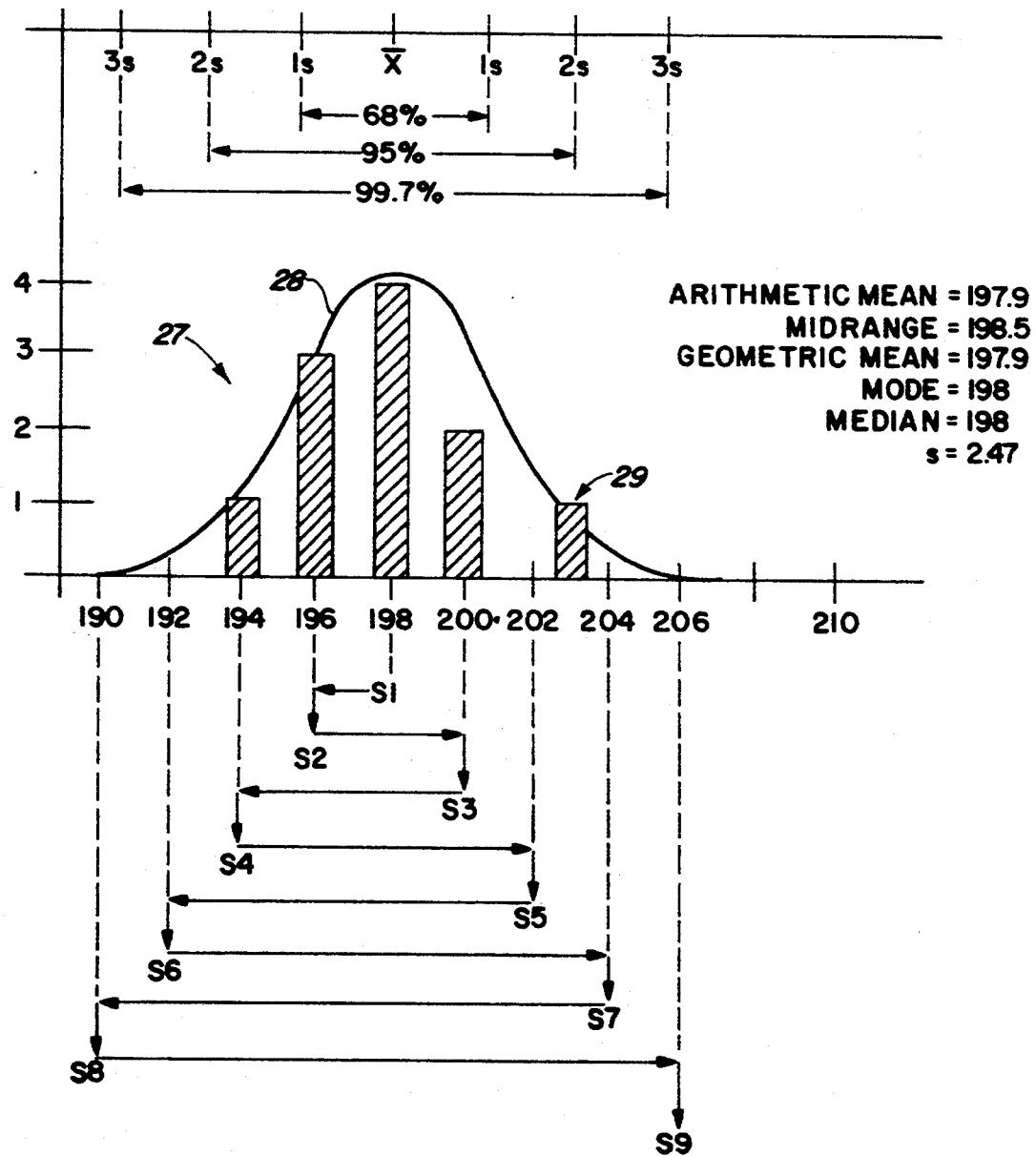
FIG. 3 illustrates the basic principles of using histograms and statistical analysis to determine a central value, a measure of variability (for use in calculating the termination window), and further illustrating the combination of symmetrical-centrifugal scanning about the computed central value according to the present invention.

If the distribution is normal (Gaussian), then under the Empirical Rule, 68% of all observations (or samples) will be within 1s, 95% of all observations will be within 2s, and 99.7% of all observations will be within 3s, as illustrated in FIG. 3. If the distribution is not normal, then under Chebyshev's inequality at least 89% of the samples will be within three standard deviations.

The present invention is directed toward a system and method for intelligently determining the tachycardia termination window using statistical analysis. For an antitachycardia termination algorithm, there are at least four parameters that are critical for a swift termination: the starting value; the sequence; and the size and the number of steps. The present invention stores a plurality of the previously successful starting values and computes a statistically significant starting value, range (or termination window size), and step size. The number of steps can be programmable or default to a predetermined value.

Statistically speaking, the results of most measurements may be considered to have a normal distribution. FIG. 3 illustrates one possible histogram 27 based on the assumption that the termination zones are concentrated soon after the refractory period 20. The familiar "bell-curve" 28 is superimposed over the histogram, illustrating that the curve is Gaussian. Somewhere within the histogram 27 will be the "last successful value." In the prior art example described in Fig. 2, the last successful value was at 203 ms, designated as point 29 in the histogram of FIG. 3. It is apparent that a more appropriate starting value would be the center value of the histogram, with the range, or termination window size, being defined by the range of the histogram. In addition, different tachycardia rates may have a histogram centered about a different central value, with wider or narrower distributions. Thus, histogram data can be stored in memory for each tachycardia rate.

By using a starting value based on a computed central value, a more statistically significant starting value should be obtained. Furthermore, by using a computed measure of variability, a more statistically significant termination window should be obtained.

Assuming that tachycardias behave in a normal (Gaussian) way, the present invention preferably utilizes the arithmetic mean, $\overline{X}$, to determine the initial critically timed interval, or starting value, for a subsequent cardiac arrhythmia, as shown in FIG. 3. However, all of the data descriptors for determining the central value discussed above could be used as the initial or starting value for the critically timed interval for a subsequent tachycardia.

Since a normal distribution is presumed, the computed range of the termination window is preferably selected to be three standard deviations wide, 3s, centered about the mean value, $\overline{X}$. However, all of the data descriptors for determining the variability of the sampled population could be used to determine the termination window.

One skilled in the programming arts could easily construct a software program to implement any of the above calculations for the central value and the measure of variability. The choice for selecting one of the above-described central values and one of the measures of variability are dictated by the hardware, software and current drain constraints. For example, a given microprocessor may be capable of calculating the mean and standard deviation, however, the processing time may make it unattractive in terms of current drain (which can significantly affect longevity). In Gaussian distributions, the arithmetic mean, the midrange, the geometric mean, the median, and the mode, all coincide to approximately the same central value. Under these conditions, the midrange, the mode, or the median, may be easier to calculate. Likewise, it may be easier to use the sampled range to determine the window size, rather than requiring a system to perform division (for computing standard deviation).

In the preferred embodiment, at least ten (10) samples are required to provide an adequate sample for analysis, and not more than twenty-five (25) are necessary. The at least ten samples can be induced at implant or gathered as they occur naturally. In one embodiment, only the last 10–25 samples may be used to track the patient's most recent physiological needs. For example, this type of "moving window" will accommodate a patient's changing drug therapy, etc. In another embodiment, the sample size would be continuously updated to include all values (up to a memory limit) to provide a more representative view of the patient's physiological condition. Thus, as the sample sizes increases, the mean, $\overline{X}$, would approach the true mean value for the whole population, $\mu$. Likewise, the estimate of the standard deviation, s, would approach the true standard deviation for the whole population, $\sigma$.

FIG. 3 also illustrates a "symmetrical-centrifugal" scan. The first stimulation pulse will be using the central value, point "S1". The second stimulation pulse will be, for example, to the left at point "S2" and then to the right at point "S3" of the central value, etc., until 99.7% of the previously successful critically timed intervals have been tried.

As mentioned earlier, the number and size of steps could be either programmable, or automatically computed by the implantable stimulation device, based on the size and the distribution of the termination window.

Presently, the state of the art is such that the shape of the distribution of successful tachycardia termination starting values is unknown. Thus, modifications of the method may be necessary to accommodate the real world. For example, it may turn out that a particular patient may have two or more accessory pathways, thereby resulting in tachycardias having different rates, refractory periods, and termination windows. Thus, the distributions may appear to be bimodal or multimodal distributions. The method may then need to be modified to collect successful critically timed intervals for each detected tachycardia rate, or for each mode. The sequence can also be modified to scan in descending order from the value that occurs most frequently through to the value that occurs the least frequently.

Figure 4:
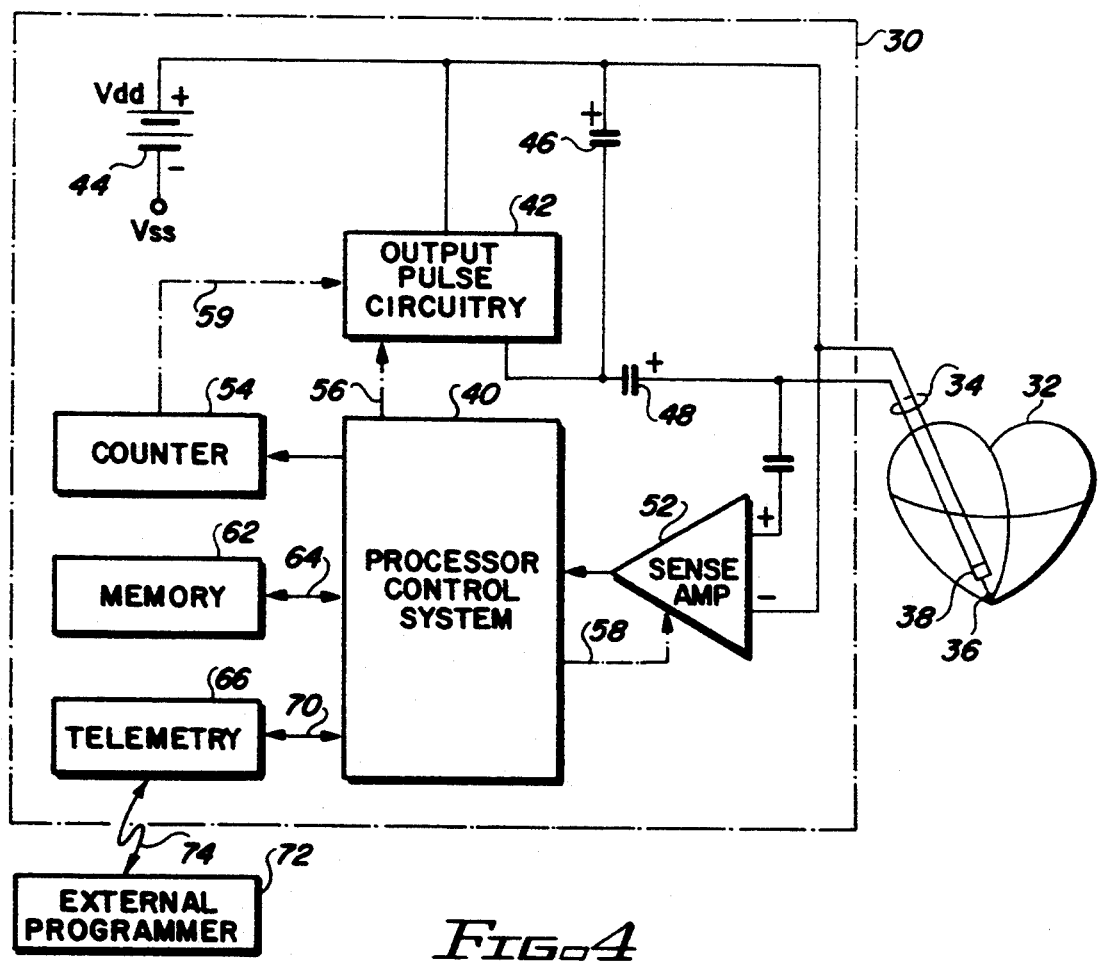
FIG. 4 is a block diagram of pulse generator circuitry that may be used within an implantable stimulation device in order to terminate a cardiac arrhythmia in accordance with the present invention.

A simplified block diagram of the pulse generator of the present invention is illustrated in FIG. 4. A pulse generator 30 is illustrated coupled to a heart 32 by way of a lead 34. The lead 34 is shown as a bipolar lead, i.e., having a tip electrode 36 and a ring electrode 38. While a single-chamber, bipolar lead system is shown, this is only to illustrate the basic functional blocks. It is understood that one skilled in the art could adapt the present invention to be used in either a dual-chamber device or with unipolar leads.

Controlling the pulse generator 30 is a processor control system 40. As is well known in the art, the processor control system 40 could be constructed from dedicated logic and timing circuitry, state machine circuitry, or a microprocessor.

Output pulse circuitry 42 generates stimulation pulses to the tip electrode 36 through the lead 34. The output pulse circuitry 42 is coupled to a battery 44 which charges a capacitor 46 to a desired or programmed value. When the capacitor 46 is fully charged, the charge is delivered to the heart 32 through an output capacitor 48. The processor control system 40 generates trigger signals to the output pulse circuitry 42 over signal line 56 to control both the rate and the inhibition of the stimulation pulses.

The processor control system 40 also controls the rate at which the output pulse circuitry 42 generates stimulation pulses, as well as keeping track of the timing of any refractory period, PVARP intervals, noise detection windows, alert intervals, etc., as is known in the art. See U.S. Pat. No. 4,712,555 (Thornander et al.) for a complete discussion on the various timing intervals.

A telemetry circuit 66 is connected to the processor control system 40 by way of a suitable command/data bus 70. In turn, the telemetry circuit 66 may be selectively coupled to an external programming device 72 by means of an appropriate communication link 74 so that desired commands may be sent to the processor control system 40 and data may be remotely received from the pulse generator 30. In this manner, noninvasive communications may be established with the implanted pulse generator 30 from a remote, external location.

The processor control system 40 is connected to a memory circuit 62 by a suitable data/address bus 64. This memory circuit 62 allows certain control parameters, used by the processor control system 40 in controlling the operation of the pulse generator 30, to be programmably stored and modified, as required, in order to customize the operation of the pulse generator 30 to suit the needs of a particular patient. Further, data sensed during the operation of the pulse generator 30 (such as, a plurality of the last successful critically timed intervals) may be stored in the memory circuit 62 for later retrieval and analysis.

A sense amplifier 52 is coupled to the lead 34 and detects the presence of cardiac activity. The sense amplifier 52 is connected to the processor control system 40 which will inhibit the output pulse circuitry 42 whenever cardiac activity is sensed in a demand fashion, as is known in the art. The sense amplifier 52 receives control signals over signal line 58 from the processor control system 40. These control signals include controlling the gain (sensitivity) and the timing of any blocking circuitry (not shown) coupled to the inputs of the sense amplifier 52.

The processor control system 40 evaluates the cardiac signal using conventional detection criteria. Typically, such means involve monitoring the heart rate to determine if the rate has exceeded a lower limit recognized by the pulse generator as a tachycardia rate. This determination is usually made over several cardiac cycles in order to avoid having a single cycle of the heart trigger a tachycardia termination mode when in fact no tachycardia has occurred. Other criteria which may be used to detect a tachycardia includes: sudden onset; rate stability; comparison of the atrial rate to ventricular rate; comparison to a physiological sensor indicated rate, etc. Discussion of such phenomena is well known in the art, and therefore will not be presented here.

At implant, a plurality of critically timed intervals will be found by inducing a plurality of tachycardias and terminating them by traditional methods, for example, shotgunning, scanning and/or using the last known successful termination value. Each time there is a successful termination of the arrhythmia, the successful critically timed interval is stored in the memory 62. After a desired number of intervals (preferably at least ten) are stored, the processor control system 40 computes a new statistically determined starting value and a new statistically determined measure of variability using one of the above-described methods. As previously discussed, the choice of which method to use is driven by the particular microprocessor, hardware or software implemented. Hereinafter, the statistically determined starting value and window size will be referred to simply as the "computed central value" and the "computed range," respectively.

Once the computed central value, CCV, and the computed range are determined, the next occurrence of an arrhythmia will initiate a first stimulation pulse, S1, at the computed central value. As used herein, the coupling interval for each of the stimulation pulses (S1, S2, S3, etc.) is measured from the last detected R-wave.

The number of stimulation pulses delivered before repeating the scan may be programmable. The size of the steps could be the computed range divided by the number of programmed stimulation pulses (and rounded to the nearest whole number and/or the nearest value in a rate table). Alternately, it may be desirable to decrease the size of the steps within one standard deviation of the central value so that more attempts are made close to the central value. The sequence of the scan would be in symmetrical-centrifugal fashion about the computed central value (CCV), that is, S1=(CCV), S2=(CCV−1 step), S3=(CCV+1 step), S4=(CCV−2 steps), S5=(CCV+2 steps), etc.

Once an arrhythmia is detected, the last detected R-wave will trigger the processor control system 40 to load the first computed central value, S1, into a down counter 54. When the down counter 54 reaches zero, the down counter 54 will trigger the output pulse circuitry 42 to deliver a stimulation pulse. The processor control system 40 will then confirm the presence or absence of the arrhythmia. If the first stimulation pulse, S1, was unsuccessful, the processor control system 40 will (in response to subsequent R-wave) load the second computed value, S2, into the down counter 54. When the down counter 54 reaches zero, the down counter 54 will again trigger the output pulse circuitry 42 to deliver a stimulation pulse. This process will continue until all the programmed number of pulses have been delivered.

The use of a down counter is done for convenience and one of skill in the art could easily derive other methods to implement the coupling of the critically timed interval to the R-wave.

If a completely different reentrant mechanism is present (i.e., having a different accessory pathway, conduction velocity or refractory periods), then it is possible that none of the most probable stimuli will be successful. Thus, the remaining portion of the alert window may be scanned using conventional scanning techniques (e.g., shifting from left to right through the remaining alert window). If the new arrhythmia recurs frequently, then the computed central value and range will, after several successful terminations, automatically shift toward a new central value and range. If the tachycardia does not terminate, then the pulse generator can repeat the scan using additional single or multiple stimuli. Additionally, the physician may program the pulse generator to provide multiple stimuli at the onset of detection.

To ensure that the system is functioning properly, histograms of the data could be presented to the physician and displayed on a screen so that the physician could quickly verify whether the distribution is normal. A histogram for purposes of the present invention would graphically represent a frequency distribution of the samples using vertical bars, the width of the bars representing the class intervals (for example, all of the previously successful critically timed intervals for a given tachycardia rate) and the height corresponding to the frequency of occurrence in each class. It is submitted that those skilled in the art can readily write software to produce the histograms, as described above.

Furthermore, this method is consistent with the finding that tachycardias with a high rate tend to have narrow termination zones. That is, the computed range for high rate tachycardias will automatically be narrower, with a computed step size proportional to the size of the computed range and the number of programmed steps desired.

Thus, in the present invention, the scan will always be centered around the statistically determined computed central value, using steps which are proportional and most successful for that particular rate and patient. Thus, the whole range of past successful termination values will be tested in order of the highest probability. Therefore, this method should have a much higher success rate than previous shotgun approaches.

It is submitted that those skilled in the art can readily fashion logic circuitry using conventional components to perform the functions of the processor control system 40 and down counter 54, as described above. Further, the processor control system 40 may be readily fashioned using conventional logic gates, latches and similar elements. Further, as is known in the art, the pulse generator and processor control logic 40 may include a microprocessor which may be programmed to provide any desired mathematical functions, parameter values, automatic adjustment of parameter values, etc.

As thus described, it is seen that the present invention provides a system and method for use with an implantable pulse generator that quickly terminates a detected a tachycardia. While the preferred embodiment has been directed toward a system for terminating a tachycardia, the present invention could be adapted for terminating other arrhythmias.

Further, such system and method minimizes the use of potentially wasteful bursts of stimulation pulses by avoiding "shotgunning" the heart in an attempt to randomly "hit" the narrow termination window. Rather, the stimulation pulses are carefully and rapidly guided to the region of susceptibility. Moreover, the present invention provides such a cardiac arrhythmia termination system and method that significantly minimizes the hunt time for the termination window for any subsequent arrhythmia. Advantageously, the search for the critically timed interval always begins at a location within the cardiac cycle that is coincident with the most probable location of the region of susceptibility.

While the invention herein disclosed has been described by means of specific embodiments and applications thereof, numerous modifications and variations could be made thereto by those skilled in the art without departing from the scope of the invention set forth in the claims. Moreover, while the preferred embodiment of the invention is to be used in combination with an implantable stimulation device, the invention could also be employed by itself as, e.g., a diagnostic arrhythmia termination system, using either implantable or external cardiac pacing and sensing apparatus.

What is claimed is:

1. An implantable stimulation system for terminating a cardiac arrhythmia, comprising:
   detection means for detecting cardiac arrhythmias;
   pulse generating means for generating stimulation pulses to the heart at a plurality of critically timed intervals within a cardiac cycle to terminate a detected cardiac arrhythmia;
   memory means for storing a plurality of previously successful critically timed intervals which have been successful in terminating a plurality of cardiac arrhythmias;
   processing means for determining a starting value for a subsequent cardiac arrhythmia based upon the plurality of previously successful critically timed intervals stored in the memory means; and
   means for triggering the pulse generating means to generate a first stimulation pulse at the starting value determined by the processing means.

2. The implantable stimulation system recited in claim 1, wherein:
   the processing means comprises means for determining a sequence of critically timed intervals in the event that the first stimulation pulse is unsuccessful at terminating the arrhythmia, the sequence being based upon the plurality of previously successful critically timed intervals stored in the memory means; and
   the triggering means comprises means for triggering the pulse generator to generate stimulation pulses to the heart according to the sequence of critically timed intervals until the cardiac arrhythmia is terminated or a desired number of pulses are delivered.

3. The implantable stimulation system recited in claim 2, wherein the sequence determining means comprises:
   means for determining a symmetrical-centrifugal scanning sequence of critically timed intervals centered about the starting value.

4. The implantable stimulation system recited in claim 2, wherein the sequence determining means comprises:
   means for ranking the plurality of previously successful critically timed intervals in order of highest frequency of occurrence; and
   means for defining the sequence of critically timed intervals as a ranked sequence of the previously successful critically timed intervals descending in order from the highest frequency of occurrence to the lowest frequency of occurrence.

5. The implantable stimulation system recited in claim 1, wherein the processing means comprises:
   means for statistically determining a central value as the starting value, the central values being based upon the plurality of successful critically timed intervals previously stored in the memory means.

6. The implantable stimulation system recited in claim 5, wherein the means for statistically determining the central value comprises:
   means for determining an average value of the plurality of previously successful critically timed intervals.

7. The implantable stimulation system recited in claim 5, wherein the means for statistically determining the central value comprises:
   means for determining an arithmetic mean value of the plurality of previously successful critically timed intervals.

8. The implantable stimulation system recited in claim 5, wherein the means for statistically determining the central value comprises:
   means for determining a geometric mean value of the plurality of previously successful critically timed intervals.

9. The implantable stimulation system recited in claim 5, wherein the means for statistically determining the central value comprises:
   means for determining a median value of the plurality of previously successful critically timed intervals.

10. The implantable stimulation system recited in claim 5, wherein the means for statistically determining the central value comprises:
    means for determining a midrange value of the plurality of previously successful critically timed intervals.

11. The implantable stimulation system recited in claim 5, wherein the means for statistically determining the central value comprises:
    means for determining a mode value of the plurality of previously successful critically timed intervals, wherein the mode value corresponds to a value of critically timed intervals which occurs most frequently.

12. The implantable stimulation system recited in claim 1, further comprising:
    means for detecting an intrinsic cardiac rate for a plurality of a cardiac arrhythmias;
    means for storing a plurality of previously successful critically timed intervals for each rate detected by the detecting means;
    wherein the processing means includes means for determining a unique starting value for each rate detected; and
    wherein the triggering means includes means for triggering the pulse generator to generate a stimulation pulse for a subsequent cardiac arrhythmia at the unique starting value corresponding to the rate of the subsequent cardiac arrhythmia.

13. The implantable stimulation system recited in claim 1, further comprising:
    means for determining a range of critically timed intervals for use in terminating a subsequent cardiac arrhythmia, the range being based upon the plurality of previously successful critically timed intervals; and
    wherein the triggering means triggers the pulse generating means to deliver a predetermined sequence of stimulation pulses within the determined range.

14. The implantable stimulation system recited in claim 13, wherein the means for determining the range comprises:
    means for determining a standard deviation value of the plurality of previously successful critically timed intervals; and
    means for defining the range as the starting value $\pm 3$ times the standard deviation.

15. The implantable stimulation system recited in claim 13, wherein the means for determining the range comprises:
    means for determining an average deviation value of the plurality of successful critically timed intervals; and
    means for defining the range as the starting value $\pm 3$ times the average deviation.

16. The implantable stimulation system recited in claim 13, wherein the means for determining the range comprises:
- means for determining a minimum and a maximum value of the plurality of previously successful critically timed intervals; and
- means for defining a lower limit and an upper limit of the range based upon the minimum and maximum values, respectively.

17. The implantable stimulation system recited in claim 13, further comprising means for transmitting the plurality of previously successful critically timed intervals to an external display device, the external device comprising:
- means for classifying the plurality of previously successful critically timed intervals into a histogram having a predetermined number of classes; and
- means for displaying the histogram, the starting value, and the range corresponding to the plurality of previously successful critically timed intervals.

18. The implantable stimulation system recited in claim 17, further comprising:
- means for displaying an arithmetic mean, a median, a midrange value, and a mode value of the plurality of previously successful critically timed intervals; and
- means for programmably selecting a starting value based upon one of the arithmetic mean, the median, the midrange, and the mode value.

19. The implantable stimulation system recited in claim 1, wherein the plurality of previously successful critically timed intervals comprises at least ten previously successful critically timed intervals.

20. An implantable stimulation device for terminating a cardiac arrhythmia, comprising:
- means for detecting cardiac arrhythmias;
- pulse generating means for generating stimulation pulses to the heart at a plurality of critically timed intervals, in a predetermined sequence, to terminate the cardiac arrhythmias;
- memory means for storing a plurality of previously successful critically timed intervals which have been successful in terminating a plurality of cardiac arrhythmias;
- means for classifying the plurality of previously successful critically timed intervals into a histogram having a predetermined number of class intervals; and
- processor means for determining a starting value for a subsequent cardiac arrhythmia based upon the histogram.

21. The implantable stimulation device recited in claim 20, wherein the predetermined sequence comprises:
- a symmetrical-centrifugal scanning sequence centered about the starting value.

22. The implantable stimulation device recited in claim 20, wherein the predetermined sequence comprises:
- a ranked scanning sequence of the previously successful critically timed intervals ranked in order of highest frequency of occurrence.

23. The implantable stimulation device recited in claim 20, wherein the processor means comprises:
- means for statistically determining a central value of the histogram as the starting value.

24. The implantable stimulation device recited in claim 23, wherein the processor means comprises:
- means for determining an average value of the histogram as the starting value.

25. The implantable stimulation device recited in claim 20, further comprising:
- means for defining a termination window based upon the range of the histogram.

26. The implantable stimulation device recited in claim 25, wherein the means for defining a termination window comprises:
- means for determining a measure of variability based upon the dispersion of the histogram; and
- means for defining the termination window as the initial critically timed value $\pm 3$ times the measure of variability.

27. The implantable stimulation device recited in claim 26, wherein the means for determining a measure of variability comprises:
- means for determining a standard deviation value of the histogram.

28. The implantable stimulation device recited in claim 26, wherein the means for determining a measure of variability comprises:
- means for determining an average deviation value of the histogram.

29. The implantable stimulation device recited in claim 25, wherein the means for defining a termination window comprises:
- means for determining a minimum and a maximum value of the histogram; and
- means for defining a lower limit and an upper limit of the termination window based upon the minimum and maximum values, respectively.

30. An implantable stimulation device for terminating a cardiac arrhythmia, comprising:
- means for detecting cardiac arrhythmias;
- pulse generating means for generating stimulation pulses to the heart at a plurality of critically timed intervals, in a predetermined scanning sequence, to terminate the cardiac arrhythmias;
- memory means for storing a plurality of previously successful critically timed intervals which have been successful in terminating a plurality of cardiac arrhythmias;
- means for statistically determining a first and a second data descriptor based upon the plurality of previously successful critically timed intervals; and
- means for triggering the pulse generator to generate stimulation pulses based upon the first data descriptor and the second data descriptor.

31. The implantable stimulation device recited in claim 30, wherein the predetermined a scanning sequence comprises:
- a symmetrical-centrifugal sequence of stimulation pulses, starting at the first data descriptor and, if unsuccessful, followed by intervals which are alternately earlier and later about the first data descriptor until all of the previously successful critically timed intervals have been tried.

32. The implantable stimulation device recited in claim 30, wherein the predetermined a scanning sequence comprises:
- a ranked sequence of stimulation pulses, starting at the first data descriptor and, if unsuccessful, followed by each critically timed interval in order of highest frequency of occurrence.

33. The implantable stimulation device recited in claim 30, wherein the statistically determined first data descriptor comprises one of an average, an arithmetic mean, a geometric mean, a median, a midrange value, or a mode value of the plurality of previously successful critically timed intervals.

34. The implantable stimulation device recited in claim 30, wherein the statistically determined second data descriptor corresponds to one of a standard deviation, an average deviation, or a sample range of the plurality of previously successful critically timed intervals.

35. A method for terminating a cardiac arrhythmia, comprising the steps of:
  detecting cardiac arrhythmias;
  generating stimulation pulses to the heart at a plurality of critically timed intervals within a cardiac cycle to terminate the cardiac arrhythmias;
  storing a plurality of previously successful critically timed intervals which have been successful in terminating a plurality of cardiac arrhythmias;
  determining a starting value for a subsequent cardiac arrhythmia based upon the plurality of previously successful critically timed intervals; and
  generating a first stimulation pulse at the starting value for a subsequent cardiac arrhythmia.

36. The method recited in claim 35, further comprising the steps of:
  determining a sequence of critically timed intervals in the event that the first stimulation pulse is unsuccessful at terminating the arrhythmia; and
  generating stimulation pulses to the heart according to the sequence of critically timed intervals until the cardiac arrhythmia is terminated or a desired number of pulses are delivered.

37. The method recited in claim 36, further comprising the step of:
  determining a symmetrical-centrifugal scanning sequence of critically timed intervals centered about the starting value.

38. The method recited in claim 36, further comprising the steps of:
  ranking the plurality of critically timed intervals in order of highest frequency of occurrence; and
  defining the sequence of critically timed intervals according to the highest frequency of occurrence.

39. The method recited in claim 36, further comprising the steps of:
  determining a range based upon the plurality of previously successful critically timed intervals; and
  generating the sequence of stimulation pulses within the determined range.

40. The method recited in claim 39, further comprising the steps of:
  determining a measure of variability based upon the distribution of the plurality of successful critically timed intervals previously; and
  defining the range as the starting value ±3 times the measure of variability.

41. The method recited in claim 35, further comprising the step of:
  statistically determining a central value based upon the plurality of successful critically timed intervals previously stored in the memory means.

42. The method recited in claim 41, further comprising the step of:
  determining a mean value of the plurality of previously successful critically timed intervals.

43. The method recited in claim 41, further comprising the step of:
  determining a mode value of the plurality of previously successful critically timed intervals.

44. The method recited in claim 41, further comprising the step of:
  determining a median value of the plurality of previously successful critically timed intervals.

45. The method recited in claim 41, further comprising the step of:
  determining a geometric mean value of the plurality of previously successful critically timed intervals.

46. The method recited in claim 41, further comprising the step of:
  determining a midrange value of the plurality of previously successful critically timed intervals.

47. The implantable stimulation system recited in claim 3, wherein the processing means comprises:
  means for statistically determining a central value as the starting value, the central value being based upon the plurality of successful critically timed intervals previously stored in the memory means.

48. The implantable stimulation device recited in claim 47, wherein the statistically determined central value comprises one of an average, an arithmetic mean, a geometric mean, a median, a midrange value, or a mode value of the plurality of previously successful critically timed intervals.

49. The implantable stimulation system recited in claim 47, wherein the means for statistically determining the central value comprises:
  means for detecting an intrinsic cardiac rate for a plurality of a cardiac arrhythmias;
  means for storing a plurality of previously successful critically timed intervals for each rate detected by the detecting means;
  wherein the processing means includes means for determining a unique central value at each detected rate; and
  wherein the triggering means includes means for triggering the pulse generator to generate a stimulation pulse for a subsequent cardiac arrhythmia at the unique central value corresponding to the rate of the subsequent cardiac arrhythmia.

50. The implatable stimulation system recited in claim 4, further comprising:
  means for detecting an intrinsic cardiac rate for a plurality of a cardiac arrhythmias;
  means for storing a plurality of previously successful critically timed intervals for each rate detected by the detecting means;
  wherein the ranking means comprises means for ranking the plurality of previously successful critically timed intervals at each detected rate, the starting value corresponding to the highest ranked critically timed interval for a desired rate; and
  wherein the triggering means includes means for triggering the pulse generator to generate a stimulation pulse for a subsequent cardiac arrhythmia at the starting value corresponding to the rate of a subsequent cardiac arrhythmia.

51. The method recited in claim 41, further comprising the step of:
  determining an average value of the plurality of previously successful critically timed intervals.

* * * * *